United States Patent
Toyama

Patent Number: 5,661,819
Date of Patent: Aug. 26, 1997

[54] CYLINDRICAL CONTAINER INNER SURFACE TESTER HAVING COMPENSATION FOR MEASUREMENTS MADE AT OBLIQUE ANGLES

[75] Inventor: Kouichi Toyama, Kanagawa, Japan

[73] Assignee: Fuji Electric Co., Ltd., Kawasaki, Japan

[21] Appl. No.: 413,087

[22] Filed: Mar. 29, 1995

[30] Foreign Application Priority Data

Mar. 29, 1994 [JP] Japan .................. 6-057948
Sep. 19, 1994 [JP] Japan .................. 6-222984

[51] Int. Cl.$^6$ .................. G06K 9/00; G01N 9/04
[52] U.S. Cl. .............. 382/142; 348/127; 250/223 B; 356/240
[58] Field of Search .................. 382/142, 141; 348/127; 250/223 B, 223 R; 356/240; 209/526

[56] References Cited

U.S. PATENT DOCUMENTS

| | | | |
|---|---|---|---|
| 5,233,199 | 8/1993 | Toyama | 250/559 |
| 5,338,000 | 8/1994 | Toyoma | 250/223 B |
| 5,412,203 | 5/1995 | Toyama | 250/223 B |
| 5,453,612 | 9/1995 | Toyama et al. | 250/223 B |

Primary Examiner—Leo Boudreau
Assistant Examiner—Bhavesh Mehta
Attorney, Agent, or Firm—Greer, Burns & Crain, Ltd.

[57] ABSTRACT

A corner area between the bottom and the side of a cylindrical container is set as a test area. An objective lens of a TV camera is mounted to form a predetermined angle with the central axis of the cylindrical container. An image is generated on the screen of an image processing device based on the image captured by the TV camera. One-dimensional position detection slits Ws1 through Ws3 normally cross the arc of the ring-shaped highlighted portion corresponding to the corner area at three points. The coordinates of the intersections P1 through P3 of the position detection slits and the highlighted portions are obtained. They are substituted in the circular equation to calculate the coordinate ($\alpha$, $\beta$) of the center of the circle 0 having the intersections P1 through P3 on its circumference. The calculated coordinate is processed as a measured position coordinate to specify the position of the test cylindrical container so that the inner surface of the test cylindrical container can be precisely checked for a defect. Thus, the exact position of the test cylindrical container can be calculated, and the existence of a defect inside the test cylindrical container can be checked precisely.

13 Claims, 14 Drawing Sheets

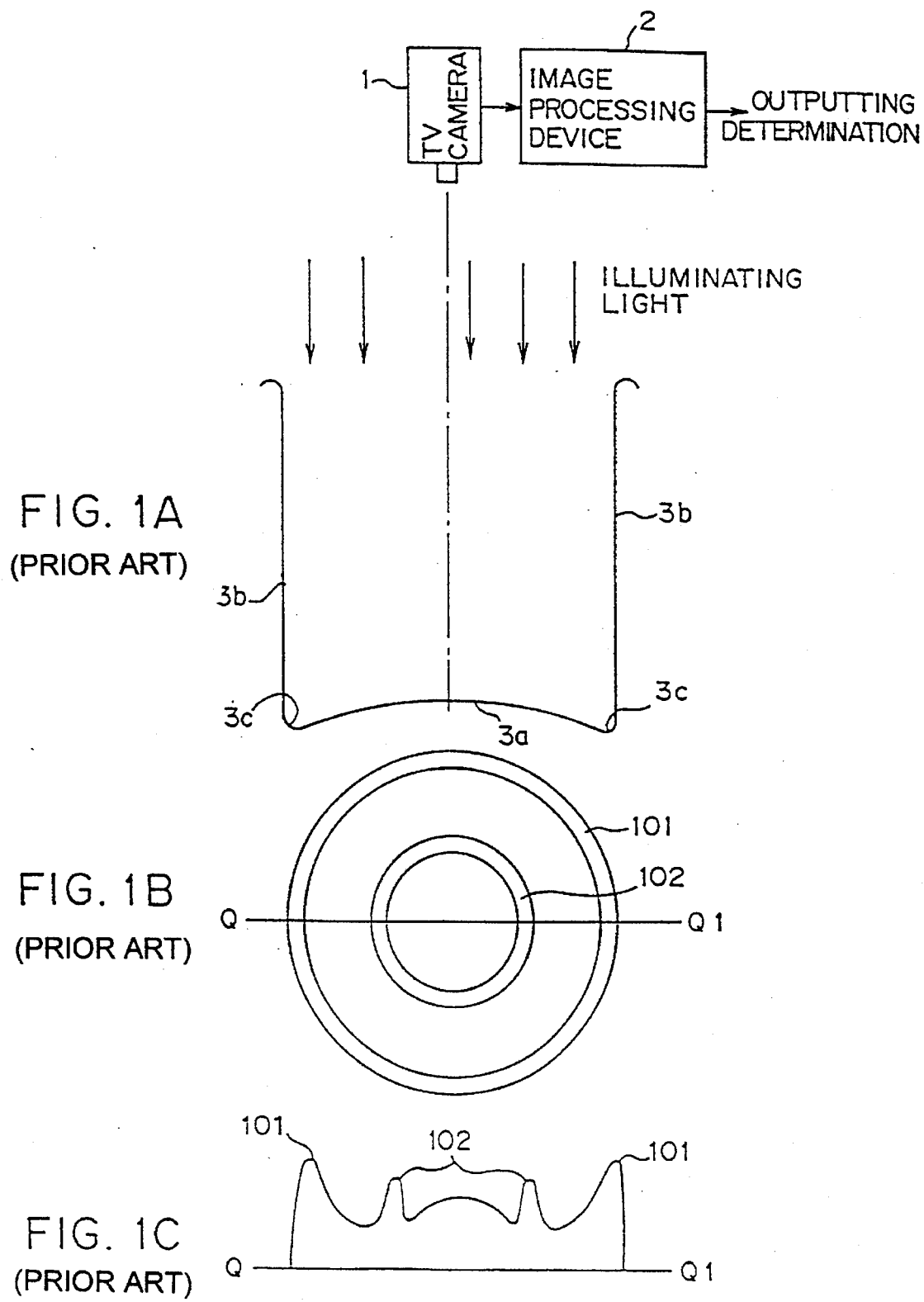

| S2 | S1 | S0 | NUMBER OF FILTERED PICTURE ELEMENTS (M) |
|----|----|----|------|
| 0 | 0 | 0 | 0 |
| 0 | 0 | 1 | 1 |
| 0 | 1 | 0 | 2 |
| 0 | 1 | 1 | 3 |
| 1 | 0 | 0 | 4 |
| 1 | 0 | 1 | — |
| 1 | 1 | 0 | — |
| 1 | 1 | 1 | — |

FIG. 6

| SEGMENT NAME | y BYTE | x BYTE | LENGTH BYTE |
|---|---|---|---|
| A | 4 | 10 | 6 |
| B | 4 | 21 | 6 |
| C | 5 | 10 | 5 |
| D | 5 | 21 | 5 |
| E | 6 | 12 | 7 |
| F | 6 | 23 | 7 |
| G | 7 | 12 | 5 |
| H | 7 | 19 | 3 |
| I | 8 | 19 | 12 |
| J | 9 | 11 | 4 |
| K | 9 | 15 | 2 |
| L | 9 | 19 | 1 |
| M | 10 | 11 | 6 |
| N | 10 | 15 | 2 |
| O | 10 | 23 | 5 |
| P | 11 | 11 | 5 |
| Q | 11 | 15 | 1 |
| R | 11 | 22 | 4 |
| S | 12 | 12 | 6 |
| T | 12 | 15 | 1 |
| U | 12 | 22 | 5 |
| V | 13 | 9 | 5 |
| W | 13 | 15 | 4 |
| X | 13 | 22 | 1 |
| Y | 14 | 7 | 3 |

FIG. 9

CYLINDRICAL CONTAINER INNER SURFACE TESTER HAVING COMPENSATION FOR MEASUREMENTS MADE AT OBLIQUE ANGLES

BACKGROUND OF THE INVENTION

1. Field of the Invention

The present invention relates to a cylindrical container inner surface tester which determines the existence of defects on the inner surface of a cylindrical container, and to, for example, a cylindrical container inner surface tester capable of detecting defects such as spots, concavity, scratches, etc. on the inner surface of a cylindrical container by transporting the cylindrical container such as an aluminum can of beer, paper cup, etc. to a checking position in a checking process, capturing the inner surface by a TV camera, storing the captured image in an image processing device, and properly processing the image.

2. Description of the Related Art

A conventional cylindrical container inner surface tester captures the inner surface of a test cylindrical container using a TV camera from the central axis of the container with the inner surface of the cylindrical container illuminated by a stroboscope light source from above the container, stores the captured static image in an image processing device, checks the existence of defects such as spots, concavity, scratches, etc. on the surface of the test cylindrical container by processing the stored static image, and determines the acceptability of the test cylindrical container. The tester is disclosed by the Patent Official Gazette Tokukaihei 5-72141 (which corresponds to U.S. Pat. No. 5,233,199) related to the application of the Applicant of the present invention.

FIGS. 1A through 1C show the outline of the conventional cylindrical container inner surface tester. The inner surface tester comprises a TV camera 1, an image processing device 2, and a stroboscope illumination light. It captures the inner surface of a cylindrical container 3 (transported by a belt conveyor to a predetermined checking position) by the TV camera 1 mounted along the central axis of the cylindrical container 3 with the cylindrical container 3 having a bottom portion as shown in FIG. 1A illuminated from above the container as shown in FIG. 1A, processes the captured static image in the image processing device 2, checks for the existence of defects such as spots, concavity, scratches, etc., and determines the acceptability of the cylindrical container 3.

FIG. 1B is a plan view of the cylindrical container 3 (can) captured by the TV camera 1. The boundary 3c between the bottom 3a and the side 3b, and the aperture of the cylindrical container 3 are illuminated and captured by the image processing device 2 as ring-shaped highlighted portions 101 and 102 in the captured image, and observed as concentric belts. FIG. 1C shows a wave form of a video signal generated while a scanning point is shifted along a raster scanning line Q-Q1 of the TV camera 1. The signal becomes a gray image signal changing according to the pattern of the highlighted portions 101 and 102.

If spots, scratches, etc. are detected on the surface of the cylindrical container 3, they absorb the illuminating light or are highlighted, thereby indicating a change in the pattern of the image. If the cylindrical container 3 is concave, the highlighted portions 101 and 102 cannot show perfect circularity. The image processing device 2 binarizes the gray image signal according to a predetermined threshold (for example, 1 if the signal indicates a level equal to or higher than the threshold, and 0 if it indicates a level lower than the threshold), differentiates the video signal and emphasizes the change in the signal to easily detect the increment or decrement in the patterns of the highlighted portions 101 and 102. Then, the image processing device 2 determines the accessibility of the cylindrical container 3 based on the above described processes. If the number and area of the defective portions exceed an allowable value, the determination result is output such that it indicates the cylindrical container as defective. Obviously, the cylindrical container determined as defective in the automatic check process is removed from the belt conveyor.

Additionally, the inner surface tester sets a plurality of test areas (windows) for a test cylindrical container, first detects the position of the cylindrical container when the container is transported to a predetermined position, corrects the difference in position through the image processing device, and generate windows at predetermined areas, thereby successfully checking defects.

The position of the test cylindrical container is checked as follows. That is, regarding the highlighted portions 101 and 102, an image signal is binarized, and then coordinates are obtained at the first rise point and the last fall point of the image signal appearing in the window along each raster scanning line. Based on the average value of the middle point of the obtained coordinates, the position of the test cylindrical container on the coordinate axis (X axis) in the scanning direction is specified. Then, the scanning direction is switched to the direction vertical to the previous scanning direction, and the position of the test cylindrical container is specified on the coordinate axis (Y axis) in the scanning direction according to the above described method. As a result, the position of the cylindrical container can be specified on a two-dimensional display screen.

Concerning the method of binarizing an image signal for use in detecting the position of a container, a difference binarization method is adopted because the gray level of an image is not so clearly displayed as to follow the fixed binarization method. For example, the binarization is based on the calculation result of the following equation (1).

$$|P(i,j)-P(i+\alpha,j)|>Thd\to 1 \tag{1}$$

where P (i,j) indicates a target picture element, P (i+α,j) indicates a background picture element α picture elements apart from the target picture element in the scanning direction, and Thd indicates a difference threshold. α can be appropriately set depending on the resolution of the image and other conditions to binarize the image stably.

If the TV camera 1 is mounted above the cylindrical container 3 to test the cylindrical container 3 by capturing the inner surface of the cylindrical container 3 from above as described above, then the side 3b of the cylindrical container 3 is observed obliquely from the mounted TV camera 1, and the side 3b may not be clearly captured. That is, the resolution of the image is deteriorated, thereby hardly detecting small defects with high precision.

As shown in FIG. 2, the TV camera 1 is mounted to form a predetermined angle θ with the central axis of the cylindrical container 3, and captures at its position an area facing the camera as a target test area. In this method, compared with the above described method by referring to FIGS. 1A through 1C, the side 3b of the cylindrical container 3 can be correctly captured, and the capabilities of resolving the picture elements of an image containing the captured portion as a test area can be highly improved, thereby successfully detecting small defects with high precision. However, checking the entire area of the inner surface of the cylindrical container in this method requires mounting a plurality of TV cameras forming different angles at the same testing position.

FIG. 2B shows the test screen generated by capturing the corner of the inner bottom of the cylindrical container from the position of the TV camera shown in FIG. 2A, enlarging the captured image, and adjusting the position of the screen relative to the X and Y axes.

If the inner surface of the cylindrical container 3 is captured obliquely from above by the TV camera 1, a part of the cylindrical container 3 gets out of the vision of the TV camera 1. Therefore, only limited parts of the ring-shaped highlighted portions 101 and 102 can be captured. Furthermore, as shown in FIGS. 2, the arcs of the highlighted portions 101 and 102 cross the lines parallel to the X and Y axes at only one point of each of the lines. Accordingly, the position of the cylindrical container 3 cannot be specified as described above by referring to FIGS. 1A through 1C (that is, specifying the position of the cylindrical container by calculating the coordinate of the middle point using the coordinates of the start and end points of the image signal crossing the scanning lines on the window screen. Thus, the exact position of the cylindrical container 3 cannot be specified.

On the other hand, if the width of the highlighted portion 102 (the corner of the inner bottom of the cylindrical container) is calculated by binarizing the image signal according to the above described equation (1), then an exact value can hardly be obtained. That is, since the scanning direction is fixed while the highlighted portion 102 is ring-shaped, a minimum true width can be obtained if the scanning line crosses the highlighted portion 101 vertically to its width. However, the extended value can be obtained from the true value by having the scanning line cross the highlighted portion 102 obliquely relative to its width. Since α is a constant, it should be set to a large value, to avoid a case where the width of the highlighted portion 102 contains both target point and a point corresponding to the constant α, thereby generating no difference for binarization and failing in calculation. This also holds true with the highlighted portion 101.

A paper cylindrical container has a seal on its side and a change in gray level on the seal may be binarized as a noise image when the image signal is binarized according to the above described equation (1). Thus, a proper method of checking the position of the cylindrical container without the above described undesirable influences is earnestly demanded.

SUMMARY OF THE INVENTION

Considering the above described problems, the present invention aims at providing an inner surface tester of a cylindrical container capable of capturing the inner surface of the cylindrical container with the objective lens facing a target point and with a predetermined angle formed from the central axis of the test cylindrical container, of exactly determining the position of the cylindrical container, and of detecting small defects on the inner surface of the cylindrical container with high precision.

The inner surface tester of a cylindrical container according to the present invention includes:

a frame memory for A/D-converting a video signal captured by a TV camera for a test area, that is, a part of the bottom and side of the cylindrical container, and storing the multivalue gray image signal as image data;

a unit for setting at least one position detection slit extending vertically to the arc of the ring-shaped area in the container, the ring-shaped area including a plurality of sampling points on the circumference of the ring-shaped area corresponding to the corner, as a test area on the test screen, between the bottom and the side of the cylindrical container, obtaining a difference gray image signal by scanning the screen data of the frame memory for each position detection slit, and binarizing the difference gray image signal according to a predetermined fixed threshold to obtain an intra-slit position detection image if the binarized value is in the test area;

a unit for obtaining an intra-slit position detection coordinate based on the picture elements crossing the ring-shaped area among the picture elements forming the intra-slit position detection image;

a unit for obtaining the coordinate of the measured position of the center of a circle formed by each of the points represented by an intra-slit position detection coordinate obtained through sampling as described above; and a unit for storing a container reference position coordinate for the coordinate of the measured position of the cylindrical container located at the container reference position.

The thus configured inner surface tester tests the inner surface of the cylindrical container by specifying the testing position of the test cylindrical container and correcting the difference in position based on the difference between the measured position coordinate and the container reference position coordinate as an offset value.

The inner surface tester also sets position detection slits at 3 or more sampling points in the ring-shaped area at the corner between the bottom and side of a cylindrical container, and calculates a measured coordinate based on the intra-slit position detection coordinate obtained for each position detection slit. Otherwise, it sets position detection slits at 2 or more sampling points in the ring-shaped area at the corner between the bottom and side of a cylindrical container, and calculates a measured coordinate based on the intra-slit position detection coordinate obtained for each position detection slit and the radius of the circle. The difference gray image signal generating unit scans screen data in the frame memory with the container reference position of the cylindrical container set as the center. Regarding the intra-slit position detection coordinate, a coordinate of a picture element which indicates the shortest distance from the container reference position of the cylindrical container among the picture elements changing from white to black when the binary image is scanned for position detection is processed as a representative point of position detection slits. Each position detection slit setting unit is designed to provide the position detection slit with the container reference position of the cylindrical container set as the center.

As a result, when the inner surface of the cylindrical container is captured by a TV camera forming a predetermined angle with the central axis, the coordinate of the center of the highlighted circle formed by each of the points containing the sampling points, that is, the measured position coordinate, is obtained by setting a position detection slit at the two or three sampling points defined on the arc of the highlighted portion of the cylindrical container within the window on the test screen, by obtaining the intra-slit position detection coordinate of the intersection of the position detection slit and the highlighted portion, and by substituting each coordinate for the circle equation. Then, the position of the test cylindrical container can be exactly specified based on the measured position coordinate.

Regarding the position detecting difference binarization signal generating unit, the bottom corner of the inner surface of the cylindrical container vertically crosses the scanning direction with the reference position of a cylindrical container centered in scanning screen data in the frame memory. Accordingly, the binarization signal can be generated stably compared with that obtained when the screen data is scanned either horizontally or vertically.

For the detection of a point on the outline of the intra-slit position detection image, the point of the position detection slit at the shortest distance from the reference position of the cylindrical container is processed as a representative point of the position detection slit. Therefore, if the slit is assigned its width, the reference position of a circle can be calculated from the representative point of each slit even if there is a joint in the side of, for example, a paper cylindrical container.

The position detection slit setting unit sets the position detection slit with the reference position of a cylindrical container set as the center (for example, in the form of a fan). Therefore, even a plurality of position detection slits can be set easily.

BRIEF DESCRIPTION OF THE DRAWINGS

FIGS. 1A, 1B, and 1C show the method of testing the inner surface of a cylindrical container. Individually, FIG. 1A shows the section of a test cylindrical container shown with the inner surface tester; FIG. 1B is the plan view of the cylindrical container captured by a TV camera; and FIG. 1C shows a video signal along the scanning line Q-Q1.

FIG. 2A shows the position of the test cylindrical container relative to the TV camera; and FIG. 2B shows the image captured by the TV camera at the position shown in FIG. 2A.

FIG. 6 shows the amount of filter data in the noise removing circuit shown in FIG. 5;

FIG. 9 shows the data stored in the coordinate memory corresponding to each segment shown in FIG. 8;

DESCRIPTION OF THE PREFERRED EMBODIMENT

The embodiment of the present invention is described below in detail by referring to the attached drawings.

Figure 3:
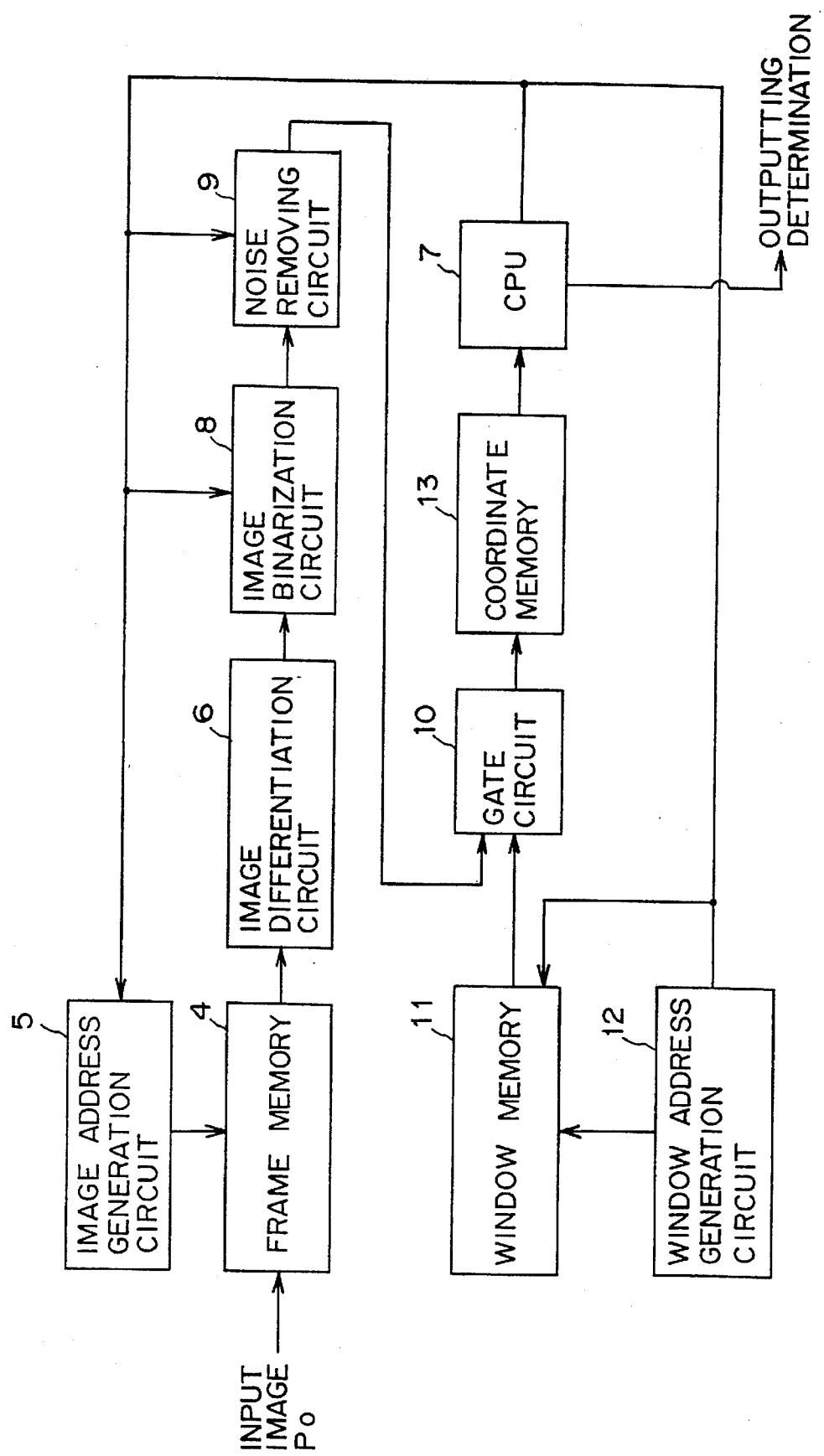
FIG. 3 is a block diagram showing the configuration of the important portion of the hardware of the cylindrical container inner surface tester according to an embodiment of the present invention.

FIG. 3 is a block diagram showing the configuration of the image processing device in the inner surface tester of a cylindrical container according to the present invention. The image processing device corresponds to the image processing device 2 shown in FIG. 1A.

An input image signal PO is converted into an 8-bit gray image signal, and the gray image signal (image data) is stored in a frame memory 4. The image data stored in the frame memory 4 is sequentially read from the frame memory 4 according to the XY address instruction for the image provided for the frame memory 4 by an image address generation circuit 5, and then transmitted to an image differentiation circuit 6. In detail, an image area of a window corresponding to a test area is set by a CPU 7. The image address generation circuit 5 designates an address such that image data in a rectangular area in the corresponding frame memory 4 is sequentially read, and the read image data is transmitted to the image differentiation circuit 6.

The image differentiation circuit 6 processes the image to obtain a difference gray image signal indicating the difference between the image data and the background gray level. The obtained image signal is output to an image binarization circuit 8 and binarized using a predetermined threshold. Then, the binarized output is transmitted to a gate circuit 10 through a noise removing circuit 9.

The gate circuit 10 receives data from a window memory 11 separate from the binarized output. The memory area selected by the window memory 11 corresponds one to one to the memory area selected according to the address signal provided by the frame memory 4. The CPU 7 controls the window memory 11 to preliminarily store 1 for the area corresponding to the test area and 0 for other areas. The data stored in the window memory 11 is read according to the address instruction provided by a window address generation circuit 12 in synchronism with the frame memory 4. That is, the read of data from the frame memory 4 and the window memory 11 indicates the synchronism of the transmitting device and the receiving device of a facsimile unit. If similar memory chips are used in the frame memory 4 and the window memory 11, then the offset of the addresses between the frame memory 4 and the window memory 11 is set by the CPU 7 such that a set of memory devices (for example, 256 megabits×8 chips) can be utilized without duplicity.

The gate circuit 10 calculates a logical product (AND) by multiplying the binarized output by the output data from the window memory 11, and the product is output to a coordinate memory 13. The coordinate memory 13 encodes the above described binarized output as described later and stores it in the memory. The CPU 7 sets the threshold and a window, corrects the difference in position, calculates for a defect, determines the acceptability, etc.

Figure 4:
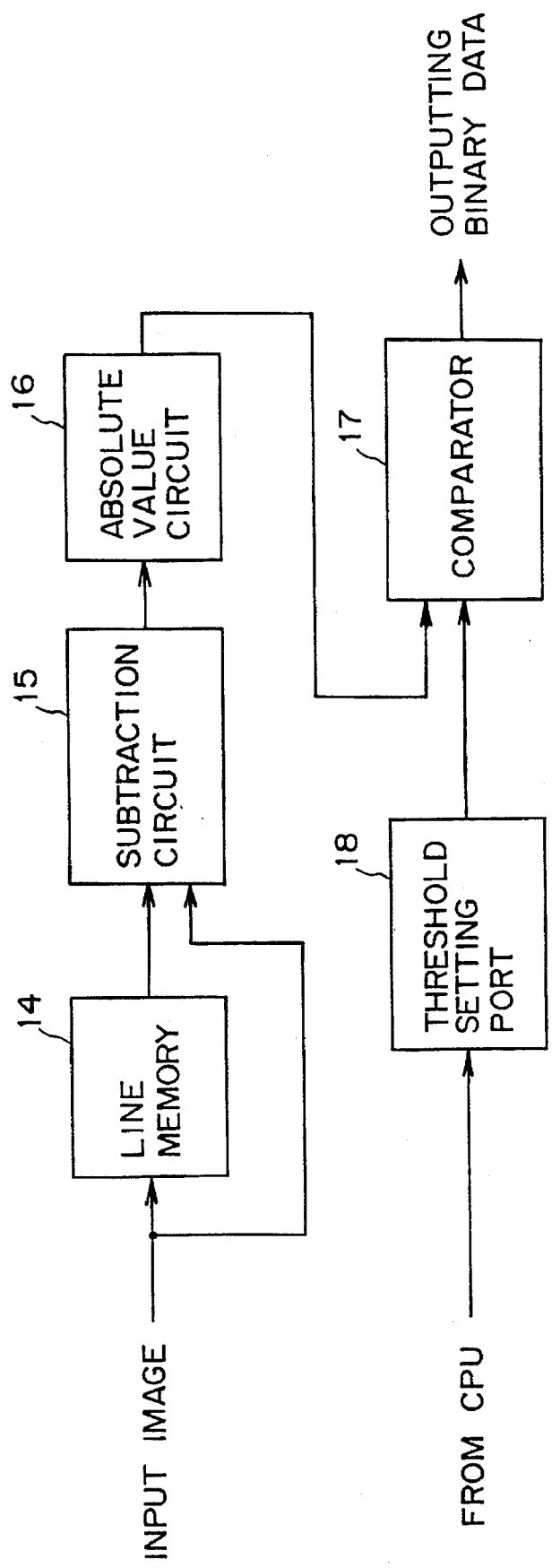
FIG. 4 is a block diagram showing in detail the configuration of the image differentiation circuit and the image binarization circuit shown in FIG. 3.

FIG. 4 is a block diagram showing in detail the configuration of the image differentiation circuit 6 and the image binarization circuit 8. The image data read from the frame memory 4 is stored in a line memory 14 and a subtraction circuit 15. Using the image data in the line memory 14 as background picture elements and the image data of the input image as target picture element data, the subtraction circuit 15 subtracts the target picture element data (value) from the background picture element data (value) and obtains the a difference gray image signal. The line memory 14 delays the picture element signal in synchronism with the picture element clock not shown in FIG. 4. The delay corresponds to the distance on the same scanning line between the background picture element and the target picture element to be processed in calculating the difference.

The output of the subtraction circuit 15 is input to the absolute value circuit 16. If the difference gray image signal is negative, then it is converted into positive and transmitted to a comparator 17. A defect detecting threshold externally input through the CPU 7 depending on the characteristics of a test cylindrical container is input to the comparator 17 through a threshold setting port 18. The threshold is compared with the difference gray image signal in the comparator 17, and transmitted to the noise removing circuit 9 shown in FIG. 3 as a binarized output.

Figure 5:
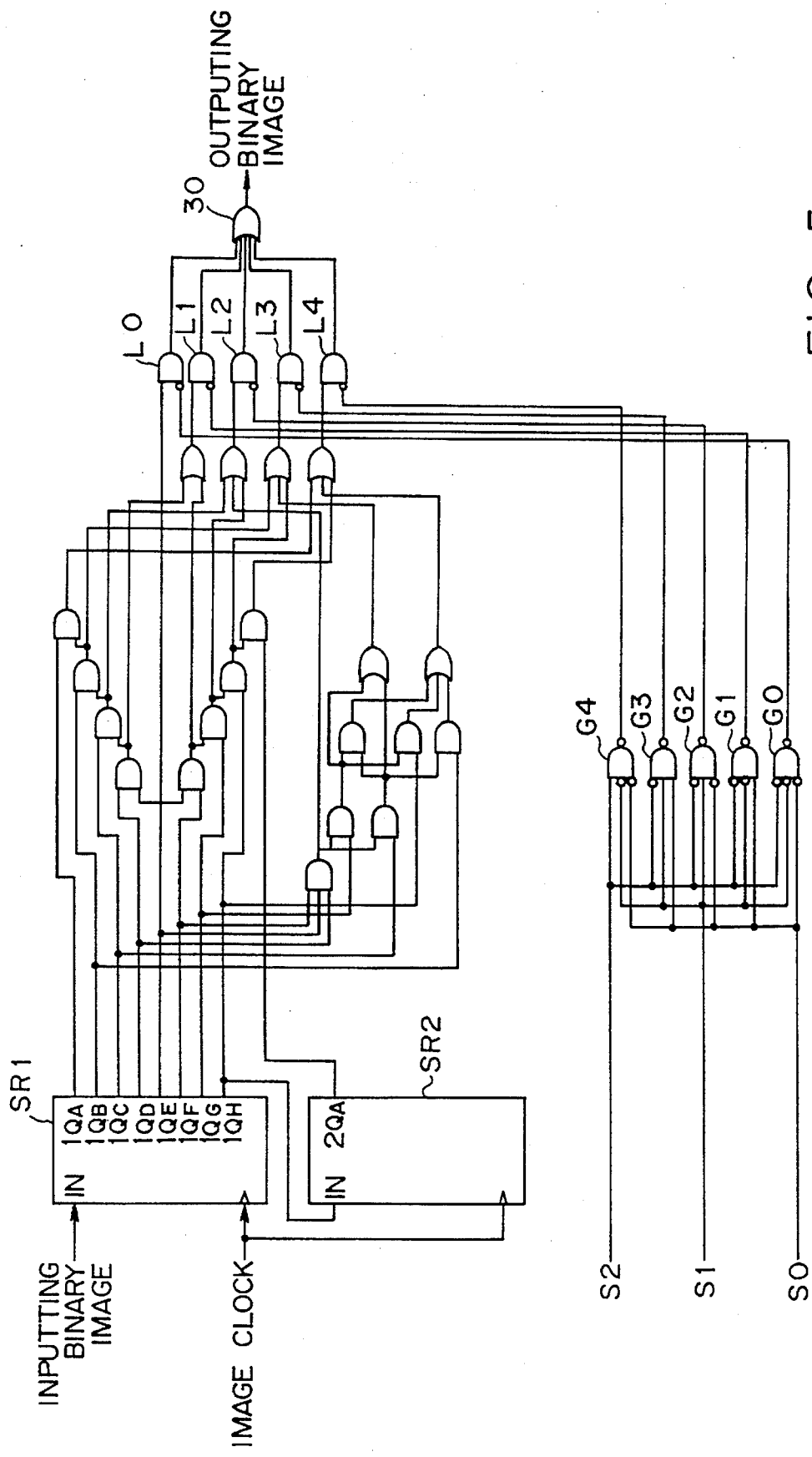
FIG. 5 shows a practical configuration of the noise removing circuit shown in FIG. 3.

FIG. 5 shows an example of the configuration of the noise removing circuit. The noise removing circuit 9 comprises shift registers SR1, SR2, and a logic circuit, functions as a picture element filter, and cuts only images each consisting of a sequence of picture elements smaller than n (n indicates a positive integer) in number on the same scanning line. That is, unless there are a sequence of the same signals (for example, 1) exceeding n picture elements on the same scanning line, the signals are ignored and not processed as image signals. The number M of the filtered picture elements can be selected from 0 through 4 (corresponding to n described above) as shown in FIG. 6 using selection signals S0–S2 to be provided for the noise removing circuit 9.

In the above described noise removing circuit, a control signal according to which gates G0 through L0 are activated is transmitted when selection signals S0, S1, and S2 are all zero. In this state, all binary image output (number of filtered picture elements: 0) delayed by 5 picture element clocks by the shift register SR (refer to FIG. 7 for information of delayed amount) is obtained from the OR gate 30.

If selection signals S2, S1, and S0 indicate 0, 0, and 1 respectively, then a control signal which activates gates G1 through L1 is transmitted. In this state, a binary image output is obtained from the OR gate 30 if a sequence of "1" appears for at least two picture elements on the same scanning line (number of filtered picture elements: 1).

If selection signals S2, S1, and S0 indicate 0, 1, and 1 respectively, then a control signal which activates gates G3 through L3 is transmitted. In this state, a binary image output is obtained from the OR gate 30 if a sequence of "1" appears for at least four picture elements on the same scanning line (number of filtered picture elements: 3).

If selection signals S2, S1, and S0 indicate 0, 1, and 1 respectively, then a control signal which activates gates G3 through L3 is transmitted. In this state, a binary image output is obtained from the OR gate 30 if a sequence of "1" appears for at least four picture elements on the same scanning line (number of filtered picture elements: 3).

Figure 7:
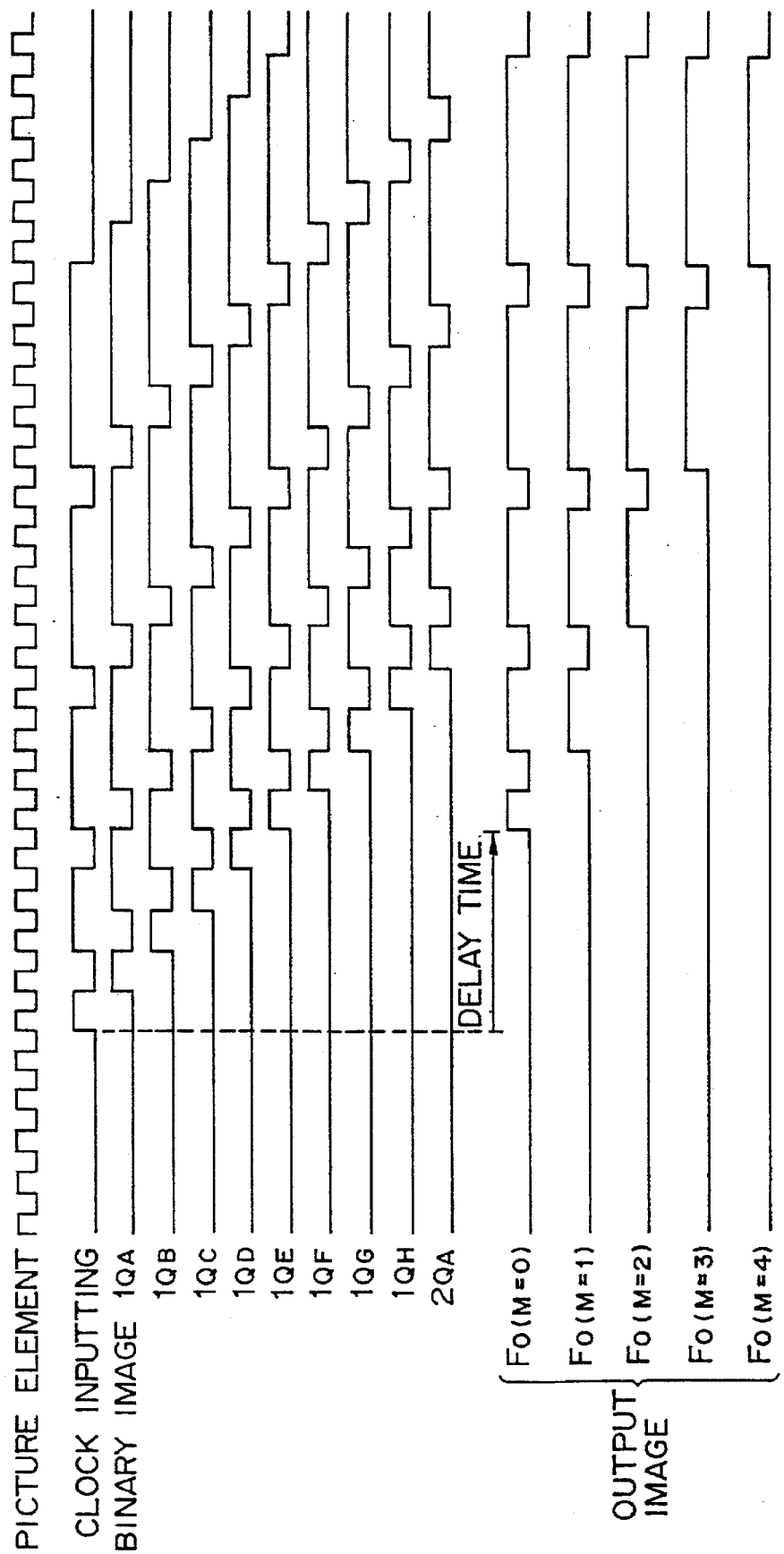
FIG. 7 is a timing chart showing the operation of the noise removing circuit shown in FIG. 5.

If selection signals S2, S1, and S0 indicate 1, 0, and 0 respectively, then a control signal which activates gates G4 through L4 is transmitted. In this state, a binary image output is obtained from the OR gate 30 if a sequence of "1" appears for at least five picture elements on the same scanning line (number of filtered picture elements: 4). FIG. 7 is a timing chart showing the operation of the noise removing circuit 9 shown in FIG. 5. The noise removing circuit 9 can have various logic circuits according to the common method to obtain binary image output from the OR gate 30 when a sequence of "0" appears for at least n picture elements on the same scanning line. Furthermore, it can be designed to obtain binary image output from the OR gate 30 if a sequence of either 1 or 0 appears for at least n picture elements on the same scanning line.

Figure 8:
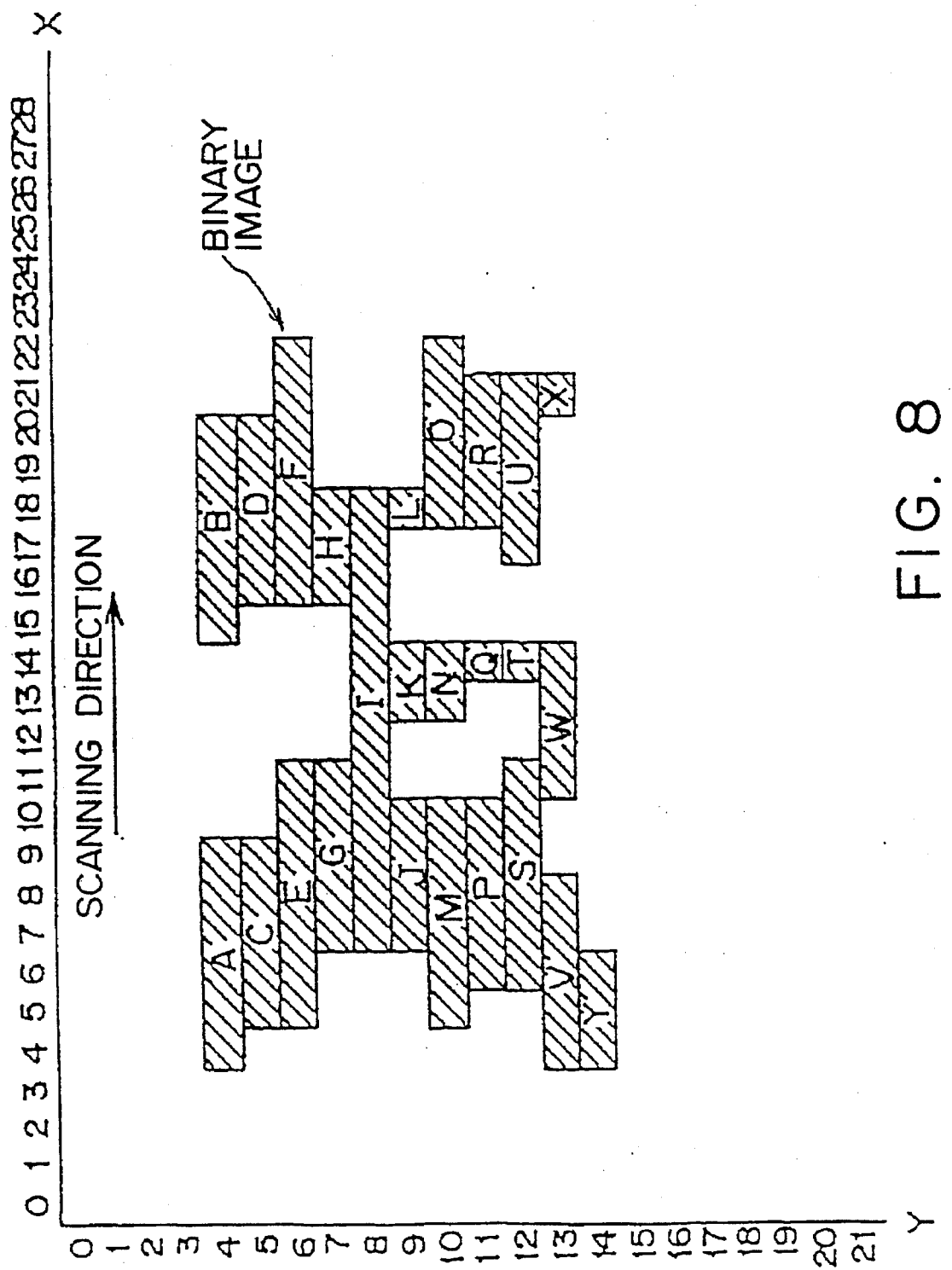
FIG. 8 shows an example of the contents of the binarized image encoded and stored in the coordinate memory shown in FIG. 3.

FIG. 8 shows the image coding process performed by the coordinate memory 13 shown in FIG. 3. A through Y shown in FIG. 8 indicate segments forming the image. In the example shown in FIG. 8, an X-axis coordinate, Y-axis coordinate, and segment length for each of the segments A through Y are stored in the coordinate memory 13 in the scanning order on the screen as shown in FIG. 9. For example, segment A ends in the 10th byte in the X direction, starts in the 4th byte in the Y direction, and is 6 bytes in length. Segment I ends in the 19th byte in the X direction, starts in the 8th byte in the Y direction, and is 12 bytes in length. The data is stored in the coordinate memory 13.

Figure 10:
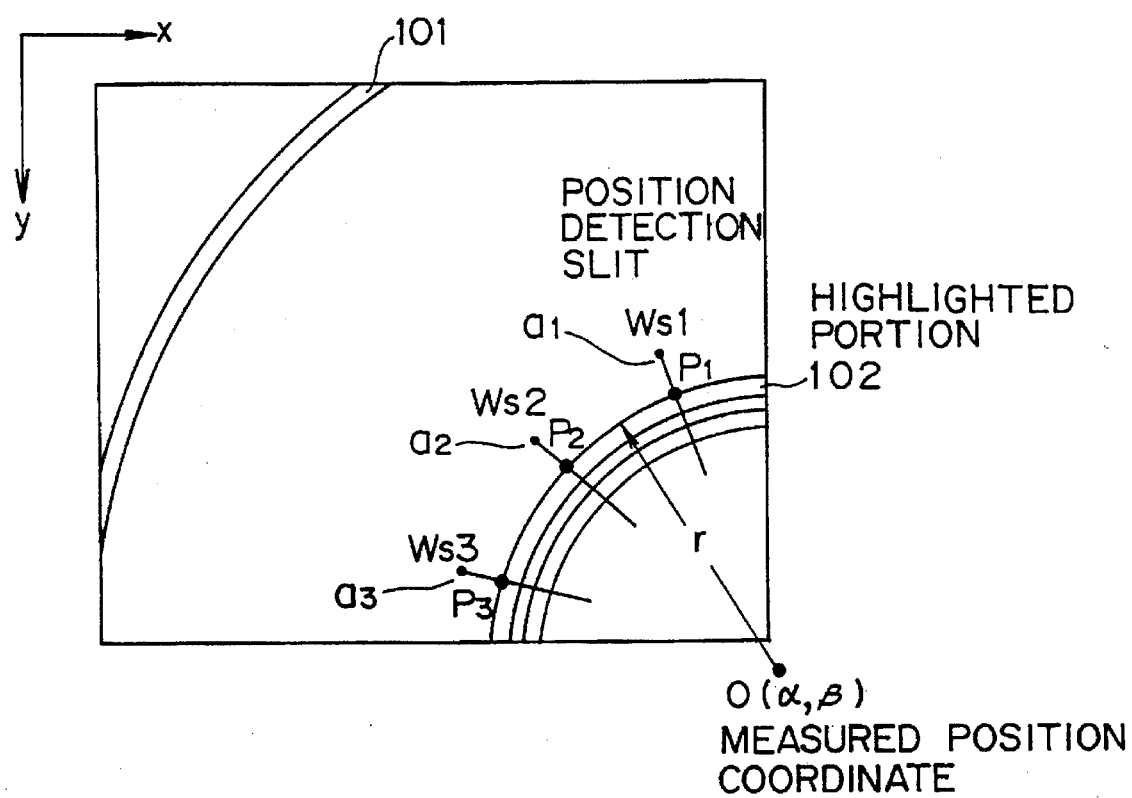
FIG. 10 shows a method of specifying the position of the test cylindrical container.
Figure 11:
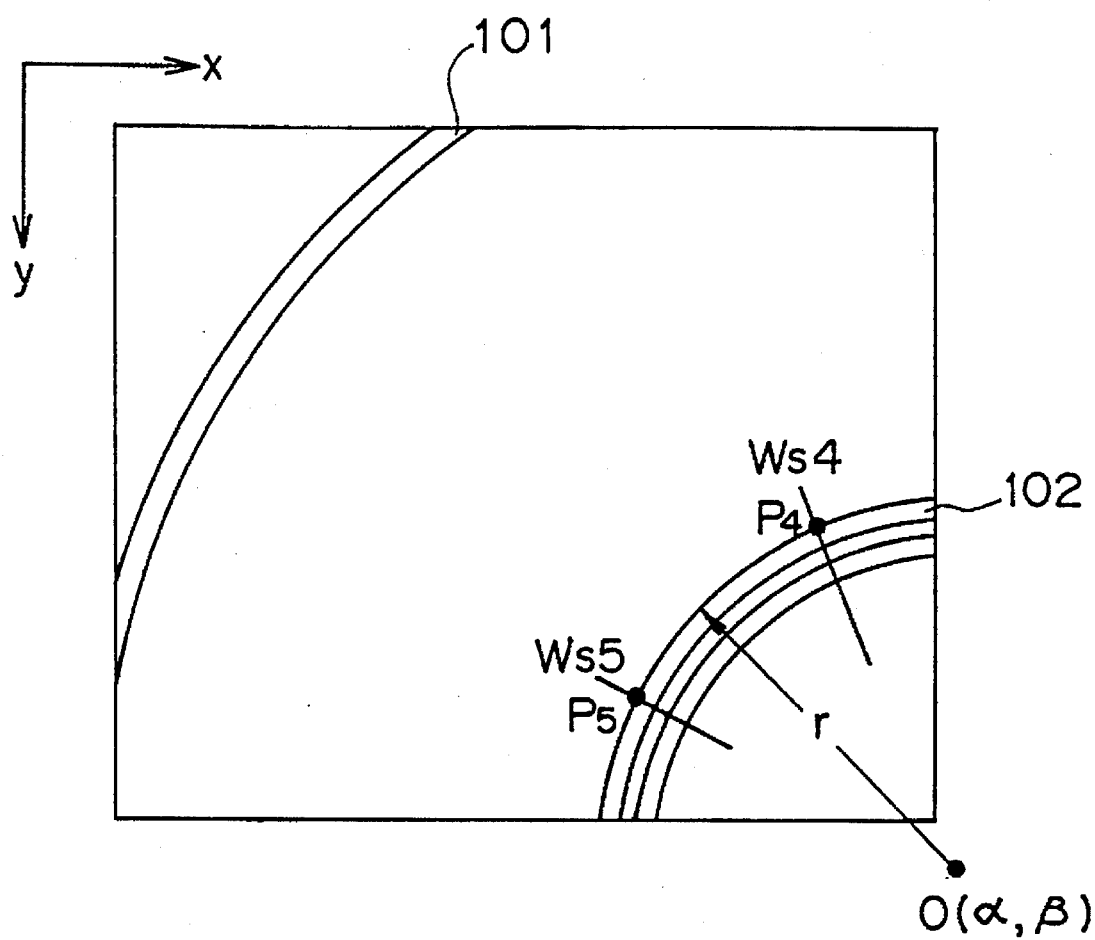
FIG. 11 shows another method of specifying the position of the test cylindrical container.

The method of specifying the position of a test cylindrical container using the cylindrical container inner surface tester including the above described image processing device is described by referring to FIGS. 10 and 11.

FIG. 10 shows the method of specifying the position of a test cylindrical container.

Figure 2A:
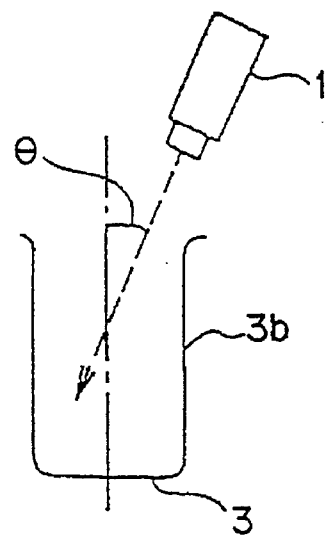
FIGS. 2A and 2B show the method of testing a cylindrical container with the TV camera mounted to form a predetermined angle with the central axis of the container and to obliquely capture the test object. Individually.
Figure 2B:
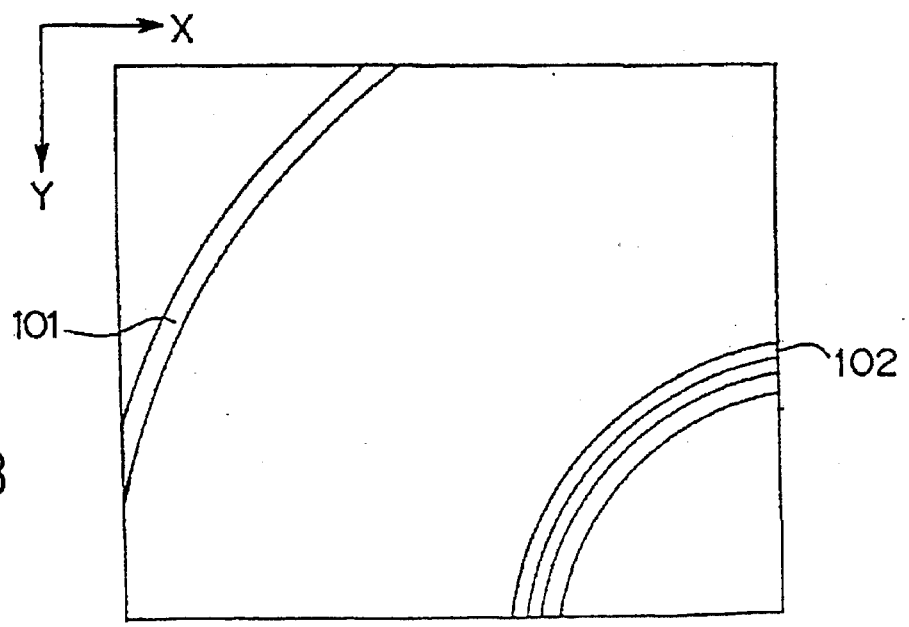

On the test screen, position detection slits WS1 through WS3 are set vertically to the arc of the ring-shaped highlighted portion 102 (highlighted pattern corresponding to the bottom corner of the cylindrical container shown in FIG. 2B) and are set to cover the three sampling points on the arc. The data defining the form of the position detection slits WS1 through WS3 is preliminarily stored in the window memory 11 shown in FIG. 3. The test cylindrical container transported to the testing position is captured by a TV camera. Then, the screen data stored in the frame memory 4 shown in FIG. 3 is scanned to obtain a binarized image signal through the image differentiation circuit 6 and the image binarization circuit 8. A container position detection image (binarized image) in each position detection slit is obtained when an AND condition is satisfied between the binarized image signal and the data defining the form of the position detection slits WS1 through WS3 read from the window memory 11. Among the intersections of the position detection slits and the difference binarized image, the coordinates (x1, y1), (x2, y2), and (x3, y3) of P1 through P3 respectively, which is the nearest to the outermost ends of the slits a1 through a3, are calculated by the CPU 7 according to the data in the coordinate memory 13 shown in FIG. 13. Then, each of the coordinates is substituted in equation (2) described later to obtain the coordinate (α, β) of the center of the circle 0 corresponding to the ring-shaped highlighted portion 102 having points P1 through P3 on its circumference. The obtained coordinate is used as a measured position detection coordinate.

$$(X-\alpha)^2+(y-\beta)^2=r^2 \qquad (2)$$

where r indicates the radius of the circle 0.

FIG. 11 shows another method of specifying the position of a test cylindrical container.

In this example, position detection slits WS4 and WS5 are set at two sampling points on the circumference of the ring-shaped highlighted portion 102 on the test screen. Then, after calculating the coordinates of points P4 and P5 as in the method shown in FIG. 10, the coordinates P4 (x4, y4) and P5 (x5, y5) and the value of the radius r are substituted in equation (2) of the circle to obtain the coordinate ($\alpha$, $\beta$) of the center of the circle 0. The obtained coordinate is used as a measured position coordinate in specifying the position of the test cylindrical container.

Additionally, the coordinate (A, B) of the circle 0 for the cylindrical container positioned at the reference testing position is obtained in the above described method and preliminarily stored in a memory as a container reference position coordinate. Then, the measured position coordinate ($\alpha$, $\beta$) is obtained on the test screen in the above described method for the test cylindrical container (whose testing position does not exactly match the container reference position) transported to the testing position in the actual test process. The measured position coordinate ($\alpha$, $\beta$) is compared with the container reference position coordinate (A, B) to calculate the deviation $\Delta x = \alpha - A$ and $\Delta y = \beta - B$. Setting $\Delta x$ and $\Delta y$ as offset values in the window address generation circuit 12 shown in FIG. 3 permits the relative position between the test image and the window for each test area to be appropriately corrected.

After the position of the test cylindrical container is checked on the test screen and the difference between the position and the container reference position is removed, a defect check is performed as described later. That is, image data is read for each window by scanning the frame memory 4 shown in FIG. 3, and picture elements indicating defective portions, that is, values larger than a predetermined threshold, are selected by the image differentiation circuit 6 and the image binarization circuit 8. Then, the number of picture elements indicating defective portions in the window screen is calculated by adding up the segment length in the coordinate memory 13 through the noise removing circuit 9 and the gate circuit 10. The acceptability of the test container is determined by comparing a threshold (allowable value) of a defective area predetermined by the CPU 7 with the number of picture elements indicating defective portions. If the number of picture elements indicating the defective portions exceeds the threshold, the CPU 7 outputs a defect determination signal as determining a defective cylindrical container. According to the determination, the defective cylindrical container 3 is removed from the belt conveyor.

Described next is an example of the method of binarizing a position testing image for a test cylindrical container.

Figure 12A:
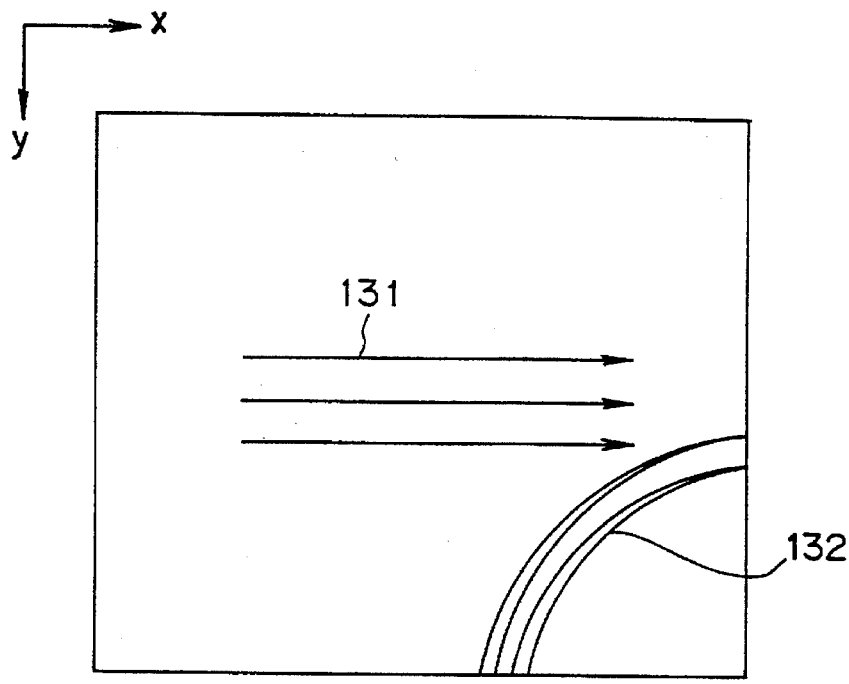
FIG. 12A shows an example of the binarized image obtained by scanning the image shown in FIG. 10 in the scanning direction 131 and applying the circular equation (2)

FIG. 12A shows an example of a binary image obtained by scanning the image shown in FIG. 10 in the scanning direction 131 and by applying the above described equation (2). As shown in FIG. 12A, the smaller the angle formed by the scanning line of a ring-shaped highlighted portion of the inner surface of the cylindrical container with the tangent to the ring-shaped highlighted portion of the inner surface of the cylindrical container is, the narrower the width of the binary image 132 becomes. Accordingly, exclusively considering this feature recommends a position detection slit set at the intersection of the scanning line and the tangent crossing each other vertically. However, in this case, the position detection slits are arranged at short intervals, and can be set within a narrow scope only, thereby enlarging the error in calculating a reference point.

Figure 12B:
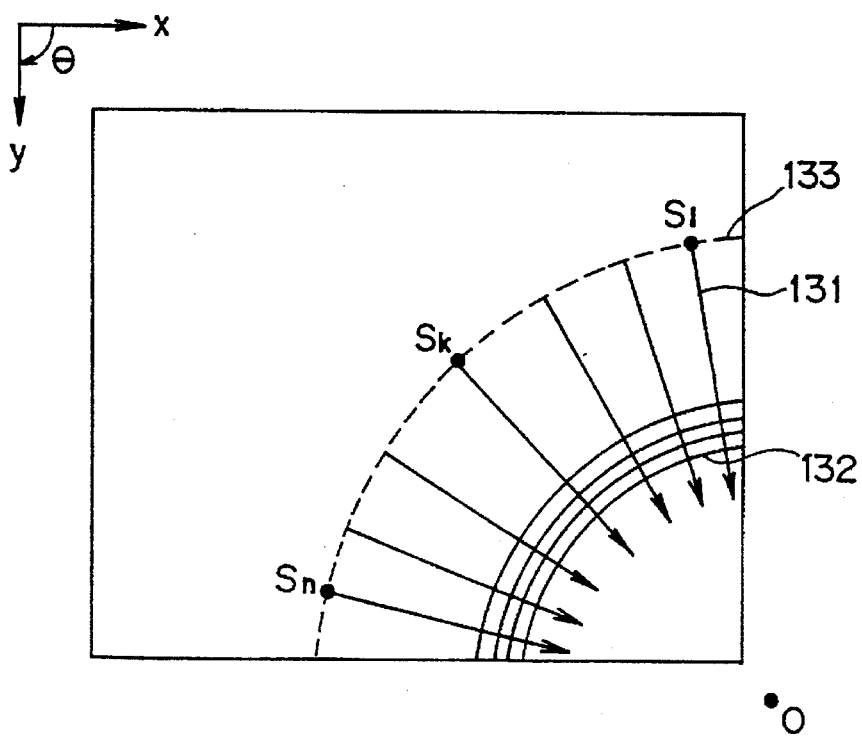
FIG. 12B shows the aspect of scanning the image shown in FIG. 10 to obtain a binarized image.

FIG. 12B shows the aspect of scanning the image shown in FIG. 10 to obtain a binary image. The scanning direction 131 is set toward the reference point 0 to obtain a given width of the binary image 132. Thus, the binary image can be obtained stably from its original image.

An arc having its radius R is set as a scan start point defining ring 133 (represented as a broken curve) from the reference point 0 to perform the above described scanning unit. Scan start points S1 through Sn are set as points on the arc at equal intervals. Scanning lines are straight lines connecting the start points to the reference point 0. Scanning lines S1 through Sn are sequentially scanned, and each of the lines is obtained as a straight line connecting the coordinates on the screen.

Described below is an example of the position detection method followed when there is a joint in the side of a cylindrical container such as a paper cylindrical container.

Figure 13A:
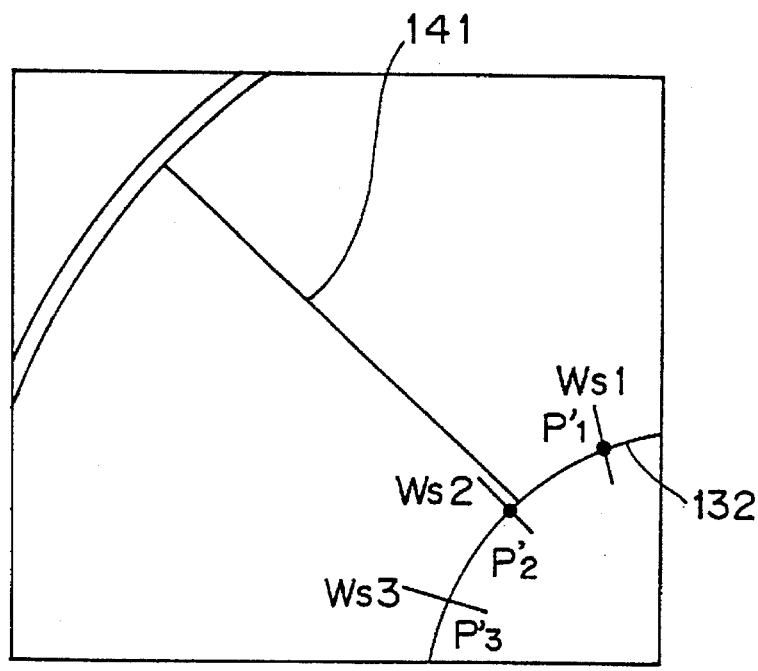
FIG. 13A shows an example of the case in which the joint 141 in the side of a paper cylindrical container is in the vision of the TV camera.
Figure 13B:
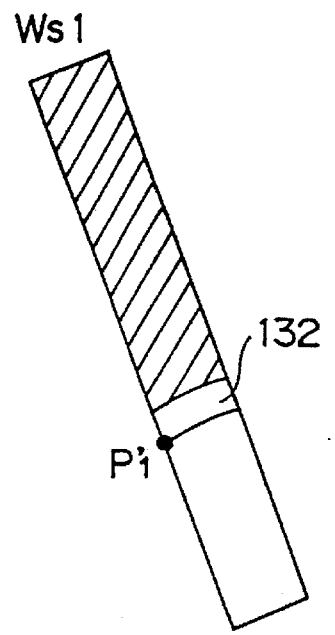
FIG. 13B shows the enlarged position detection slit Ws1.

FIG. 13A shows an example of the position detecting method followed when a joint 141 in the side of a paper cylindrical container is observed within the vision of a TV camera for capturing a test image. FIG. 13B is an enlarged image of the position detection slit $W_s1$. The binary image 132 of the ring-shaped highlighted portion inside a cylindrical container is obtained as indicated by the number 132. The joint is not located at a predetermined position on the side of the cylindrical container, but appears at a variable position. Accordingly, it may appear in the shadowed area. If a binary image is scanned for position detection to obtain the representative point in the position detection slit $W_s1$ regardless of the existence of the joint, the coordinates of change points from white to black are stored. Among the coordinates of the change points, change point P'1 indicating the shortest distance to the container position reference point 0 is defined as the representative point of the position detection slit $W_s1$. Thus, the existence of the joint 141 in the shadowed area shown in FIG. 13B has no influence on position detection.

Using this method, the coordinates of change points P'2, P'3, etc. at the corner between the side and the bottom of the test cylindrical container are obtained, thereby calculating the position of the center of the cylindrical container.

Then, described below is the method of setting a position detection slit.

Figure 14:
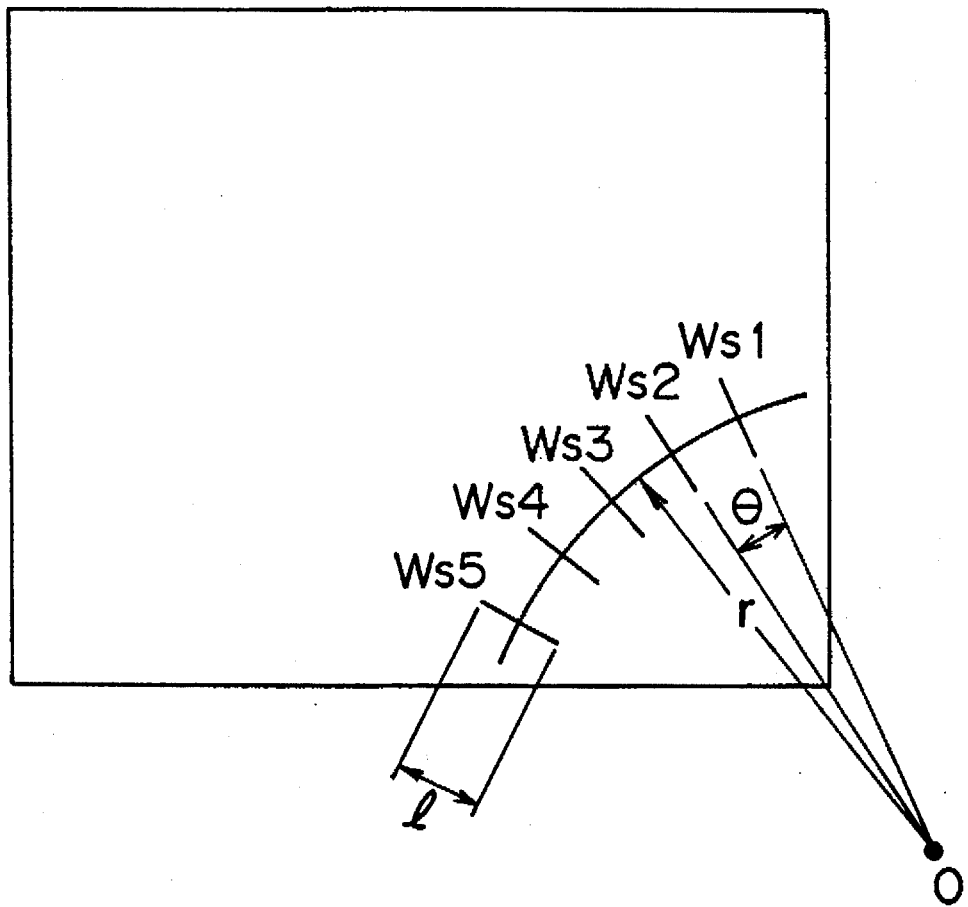
FIG. 14 shows an example of the position detection slits Ws1 through Ws5 set on the screen.

FIG. 14 shows an example of setting position detection slits $W_s1$ through $W_s5$ on the screen. They can be defined by specifying the number n of position detection slits; container reference position 0 outside the screen; distance r from the container reference position 0 to the center of the position detection slit; interval of the position detection slit $\theta$; and length l of the position detection slit. Therefore, it is more effective to simultaneously generate position detection slits by specifying these parameters than to set each position detection slit.

As described above, the present invention can correctly specify the position of a test cylindrical container on the test screen even when the inner surface of a test cylindrical container is captured by a TV camera from a point forming a specified angle with the central axis of the cylindrical container. Based on this, the position discrepancy can be corrected and very small defects inside a test cylindrical container can be detected with precision. Thus, the precision in testing the inner surface of the side of the test cylindrical container can be greatly improved, thereby enhancing the capabilities of the tester and applicability of the general-purpose tester.

What is claimed is:

1. A cylindrical container inner surface tester which checks an inner surface of a cylindrical container having a bottom for spots, scratches, and other defects and determines acceptability of the cylindrical container by capturing by a TV camera the inner surface from above obliquely to a central axis of the cylindrical container, stores a captured image in an image processing device, corrects a position of the image in the image processing device, and processes the image displayed in a window set corresponding to a test area of the cylindrical container, comprising:

a frame memory for A/D-converting a video signal captured by the TV camera for the test area which is a part of the bottom and a side of the cylindrical container, and storing a multivalue gray image signal as screen data;

means for setting at least one position detection slit extending vertically to an arc of a ring-shaped area in the container, the ring-shaped area including a plurality of sampling points on a circumference of the ring-shaped area corresponding to a corner, as the test area on a test screen, between the bottom and the side of the cylindrical container, obtaining a difference gray image signal by scanning screen data of said frame memory for each position detection slit, and binarizing the difference gray image signal according to a predetermined fixed threshold to obtain an intra-slit position detection image if the binarized difference gray image signal value is in the window set;

means for obtaining an intra-slit position detection coordinate based on picture elements crossing the ring-shaped area among the picture elements forming the intra-slit position detection image;

means for obtaining a coordinate of a measured position of a center of a circle formed by each point represented by an intra-slit position detection coordinate obtained through sampling; and means for storing a container reference position coordinate for a coordinate of the measured position of the center of the circle located at the container reference position, a thus configured inner surface tester testing the inner surface of the cylindrical container by specifying the test position of the test cylindrical container and correcting a difference in position based on the difference between the measured position coordinate and the container reference position coordinate as an offset value.

2. The cylindrical container inner surface tester according to claim 1, wherein position detection slits are set at 3 or more sampling points in the ring-shaped area at the corner between the bottom and side of the cylindrical container, and the tester calculates the measured coordinate based on the intra-slit position detection coordinate obtained for each position detection slit.

3. The cylindrical container inner surface tester according to claim 2, further comprising:

difference gray image signal generating means for scanning the screen data in said frame memory with the container reference position of the cylindrical container set as a center.

4. The cylindrical container inner surface tester according to claim 3, further comprising:

difference gray image signal generating means for scanning the screen data in said frame memory with the container reference position of the cylindrical container set at a center.

5. The cylindrical container inner surface tester according to claim 3, wherein regarding the intra-slit position detection coordinate, a coordinate of a picture element which indicates a shortest distance from the container reference position of the cylindrical container among the picture elements changing from white to black when a binary image is scanned for position detection is processed as a representative point of the position detection slits.

6. The cylindrical container inner surface tester according to claim 3, further comprising:

position detection slit setting means designed to provide the position detection slit with the container reference position of the cylindrical container set as a center.

7. The cylindrical container inner surface tester according to claim 2, wherein regarding the intra-slit position detection coordinate, a coordinate of a picture element which indicates a shortest distance from the container reference position of the cylindrical container among the picture elements changing from white to black when a binary image is scanned for position detection is processed as a representative point of the position detection slits.

8. The cylindrical container inner surface tester according to claim 2, further comprising:

position detection slit setting means designed to provide the position detection slit with the container reference position of the cylindrical container set as a center.

9. The cylindrical container inner surface tester according to claim 1, wherein said position detection slits are set at 2 or more sampling points in the ring-shaped area at the corner between the bottom and side of the cylindrical container, and the tester calculates the measured coordinate based on the intra-slit position detection coordinate obtained for each position detection slit and a radius of a related circle.

10. The cylindrical container inner surface tester according to claim 1, further comprising:

difference gray image signal generating means for scanning the screen data in said frame memory with the container reference position of the cylindrical container set as a center.

11. The cylindrical container inner surface tester according to claim 1, wherein regarding the intra-slit position detection coordinate, a coordinate of a picture element which indicates a shortest distance from the container reference position of the cylindrical container among the picture elements changing from white to black when a binary image is scanned for position detection is processed as a representative point of the position detection slits.

12. The cylindrical container inner surface tester according to claim 1, further comprising:

position detection slit setting means designed to provide the position detection slit with the container reference position of the cylindrical container set as a center.

13. A container inner surface tester which checks an inner surface of a container having a bottom for defects and determines acceptability of the container by capturing the inner surface from above obliquely to a central axis of the cylindrical container, stores a captured image in an image processing device, correcting a position of the image in the image processing device, and processing the image displayed in a window set corresponding to a test area of the container, comprising:

means for A/D-converting a video signal for the test area which is a part of the bottom and a side of the container, and storing a multivalue gray image signal as screen data;

means for setting a position detection slit extending vertically to an arc of a ring-shaped area including a plurality of sampling points on a circumference of the ring-shaped area corresponding to a corner, as the test area on a test screen, between the bottom and the side of the container, obtaining a difference gray image signal by scanning said screen data for each position slit, and binarizing it according to a predetermined fixed threshold to obtain an intra-slit position detection image if the binarized value is in the window set;

means for obtaining an intra-slit position detection coordinate based on picture elements crossing the ring-shaped area among the picture elements forming an intra-slit position detection image;

means for obtaining a coordinate of a measured position of a center of a circle formed by each point represented by an intra-slit position detection coordinate obtained through sampling; and means for storing a container reference position coordinate for a coordinate of the measured position of the container located at the container reference position, a thus configured inner surface tester testing the inner surface of the container by specifying the test position of the test container and correcting a difference in position based on the difference between the measured position coordinate and the container reference position coordinate as an offset value.

* * * * *